(12) United States Patent
Miller (10) Patent No.: US 8,298,266 B2
(45) Date of Patent: Oct. 30, 2012

(54) CONNECTORS FOR ELONGATED SURGICAL MEMBERS AND METHODS OF USE

(75) Inventor: Keith Miller, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1204 days.

(21) Appl. No.: 12/101,693

(22) Filed: Apr. 11, 2008

(65) Prior Publication Data
US 2009/0259256 A1    Oct. 15, 2009

(51) Int. Cl.
*A61B 17/70* (2006.01)
(52) U.S. Cl. .................................................. 606/250
(58) Field of Classification Search ............ 606/53–60, 606/246–278
See application file for complete search history.

(56) References Cited

U.S. PATENT DOCUMENTS

| | | | |
|---|---|---|---|
| 5,060,635 A | 10/1991 | Steür et al. | |
| 5,312,405 A | 5/1994 | Korotko et al. | |
| 5,370,696 A | 12/1994 | Jamison et al. | |
| 5,601,552 A | 2/1997 | Cotrel | |
| 5,649,926 A | 7/1997 | Howland | |
| 5,947,966 A | 9/1999 | Drewry et al. | |
| 6,030,389 A | 2/2000 | Wagner et al. | |
| 6,234,705 B1 | 5/2001 | Troxell | |
| 6,283,967 B1 | 9/2001 | Troxell et al. | |
| 6,306,137 B2 | 10/2001 | Troxell | |
| 6,454,769 B2 | 9/2002 | Wagner et al. | |
| 6,736,817 B2 | 5/2004 | Troxell et al. | |
| 6,875,211 B2 | 4/2005 | Nichols et al. | |
| 6,989,011 B2* | 1/2006 | Paul et al. | 606/250 |
| 7,104,993 B2 | 9/2006 | Baynham et al. | |
| 7,137,986 B2 | 11/2006 | Troxell et al. | |
| 7,806,913 B2* | 10/2010 | Fanger et al. | 606/260 |
| 2001/0047171 A1 | 11/2001 | Troxell et al. | |
| 2002/0052603 A1 | 5/2002 | Nichols et al. | |
| 2004/0053198 A1 | 3/2004 | Minevski et al. | |
| 2004/0053199 A1 | 3/2004 | Minevski et al. | |
| 2004/0142063 A1* | 7/2004 | Kolz | 425/298 |
| 2004/0176765 A1* | 9/2004 | Troxell et al. | 606/61 |
| 2004/0237847 A1 | 12/2004 | Axen et al. | |
| 2005/0192569 A1 | 9/2005 | Nichols et al. | |
| 2005/0228378 A1* | 10/2005 | Kalfas et al. | 606/61 |
| 2006/0009766 A1 | 1/2006 | Lee et al. | |

(Continued)

FOREIGN PATENT DOCUMENTS
EP    637437 A1    8/1995

OTHER PUBLICATIONS

International Search Report, Nov. 3, 2009.

*Primary Examiner* — Eduardo C Robert
*Assistant Examiner* — James Palmer (57) ABSTRACT

The present application relates to connectors for coupling together two surgical members of different materials while inhibiting galvanic corrosion. The connector may include a first coupling element composed of a material with a similar galvanic potential to one of the surgical members, and a second coupling element composed of a material with a similar galvanic potential to the second surgical member. Each of the first and second coupling elements may be configured to connect to the respective surgical member. The connector may also include a coupling medium disposed between the first and second coupling elements. The coupling medium may function to connect together the two coupling elements, and isolate the coupling elements to inhibit galvanic corrosion.

23 Claims, 6 Drawing Sheets

U.S. PATENT DOCUMENTS

| | | |
|---|---|---|
| 2006/0276787 A1 | 12/2006 | Zubok et al. |
| 2006/0293670 A1 | 12/2006 | Smisson, III et al. |
| 2007/0016193 A1 | 1/2007 | Ritland |
| 2007/0118122 A1 | 5/2007 | Butler et al. |
| 2007/0276373 A1* | 11/2007 | Malandain ............... 606/61 |
| 2008/0234743 A1 | 9/2008 | Marik |
| 2009/0143823 A1* | 6/2009 | Jeon et al. ............... 606/250 |
| 2009/0228044 A1* | 9/2009 | Jeon et al. ............... 606/254 |
| 2009/0228046 A1* | 9/2009 | Garamszegi ............... 606/278 |

* cited by examiner

CONNECTORS FOR ELONGATED SURGICAL MEMBERS AND METHODS OF USE

BACKGROUND

The present application relates to a device and methods for connecting elongated surgical members, and in particular, to methods and connectors that allow elongated surgical members of different materials to be attached together while inhibiting galvanic corrosion.

It is often necessary to surgically treat disorders such as scoliosis and broken bones with two or more elongated surgical members. The elongated members, typically either rods or plates, are placed along the area to be treated, such as the broken bone or the vertebral column. The elongated members may be attached with various attachment devices, such as screws, hooks, and various other types of fasteners.

It is well known that the strength and stability of a dual member assembly can be increased by coupling the members with a connector that transversely connects to the longitudinal axes of the members. Specifically, the two members are parallel to each other and may overlap, or may be in an end-to-end configuration.

Biocompatible materials are used for the members but, however, due to corrosion concerns, members of different materials are rarely connected together. The corrosion resistance commonly referred to in the art is against direct chemical attack, which in the body means a slow erosion of the material by acids which dissolve the material. It is well known that most body fluids that bathe implants are acidic. The biocompatible metals dissolve extremely slowly in the body. Polymers are even more resistant to acidic attack.

A second type of corrosion is electro-chemical, also called galvanic corrosion. Every metal is conductive and has a distinct electro-chemical potential, i.e., voltage when immersed in an acidic or saline environment. A battery is created when two such metals are introduced in a common bath, and then connected together. One metal becomes an electron donor and dissolves, and the other becomes an electron receptor and adds material (a compound of the donor and the bath materials). Galvanic corrosion is a serious problem when metals of different galvanic potential are combined in a common medium and in close proximity to each other.

Generally, galvanic corrosion is avoided by using members of only one type of metal. However, this limits the choice of a plurality of metals of different properties when desired, such as stress resistance, elasticity, hardness, and so forth. Further, if two different members are close to one another, a battery action can be made if there is some contact, such as anchors and plates and so forth.

Therefore, devices and methods are needed that would allow the elongated surgical members to be connected together while inhibiting galvanic corrosion.

SUMMARY

The present application relates to connectors for coupling together two surgical members of different materials while inhibiting galvanic corrosion. The connector may include a first coupling element composed of a material with a similar galvanic potential to one of the surgical members, and a second coupling element composed of a material with a similar galvanic potential to the second surgical member. Each of the first and second coupling elements may be configured to connect to the respective surgical member. The connector may also include a coupling medium disposed between the first and second coupling elements. The coupling medium may function to connect together the two coupling elements, and isolate the coupling elements to inhibit galvanic corrosion.

DETAILED DESCRIPTION

Figure 1:
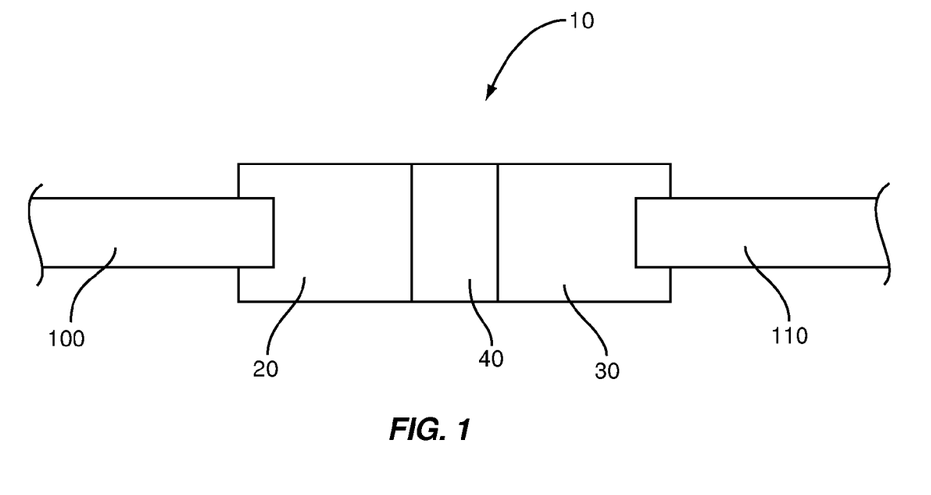
FIG. 1 is a schematic representation of a connector positioned between first and second members according to one embodiment.

The present application is directed to devices and methods for connecting together surgical members of different materials and inhibiting galvanic corrosion. FIG. 1 illustrates a schematic representation of a connector 10 that connects together first and second members 100, 110. The connector 10 includes a first coupling element 20 that connects to and includes the same or similar galvanic potential as the first member 100. The connector 10 also includes a second coupling element 30 that connects to and includes the same or similar galvanic potential as the second member 110. A coupling medium 40 is positioned between the first and second coupling elements 20, 30. The coupling medium 40 connects together the two coupling elements 20, 30 and insulates the two members 100, 110 to inhibit a galvanic couple from being established when the members 100, 110 are positioned within a patient.

A function of the connector 10 is to connect two members 100, 110 of different galvanic potentials. The connector 10 performs this function by physically separating the two members 100, 110 with one or more inert materials, or by one or more intermediate galvanic materials.

Figure 2:
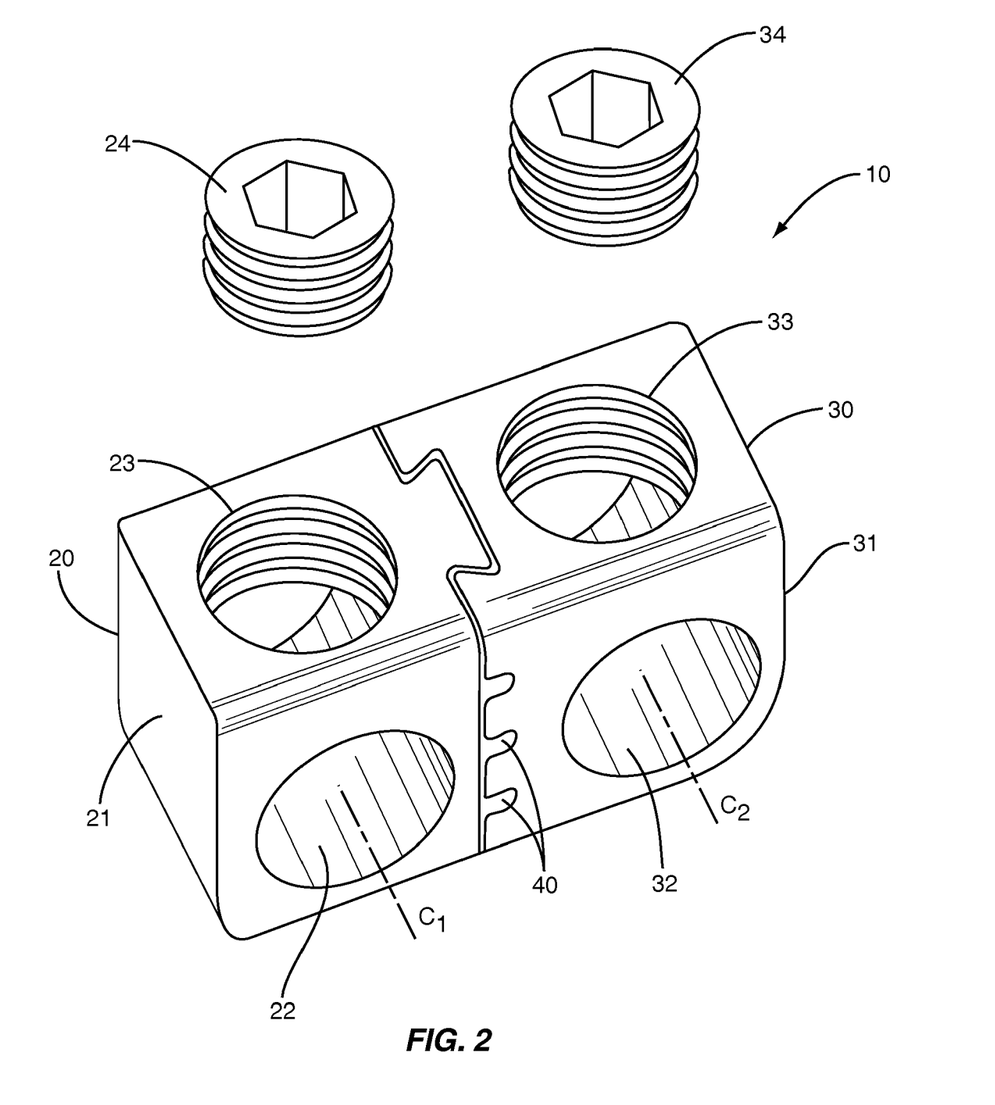
FIG. 2 is a perspective view of a connector constructed according to one embodiment.

FIG. 2 illustrates one embodiment of a connector 10 with a first coupling element 20, second coupling element 30, and a coupling medium 40. The first coupling element 20 includes a body 21 with a first opening 22 sized to receive the first member 100. A second opening 23 extends through the body 20 from a different direction and extends into the first opening 22. A constraining member 24 is sized to fit within the second opening 23 and extend into the first opening 22 to contact against and constrain the first member 100 with the body 21. The first section 20 is constructed of a material that includes the same or substantially the same galvanic potential as the first member 100.

Similarly, the second coupling element 30 includes a body 31 with a first opening 32 sized to receive the second member 110. A second opening 33 extends through the body 31 from a different direction and extends into the first opening 32. A constraining member 34 is sized to fit within the second opening 33 and extend into the first opening 32 to contact against and constrain the second member 110 with the body 31. The second section 30 is constructed of a material that includes the same or substantially the same galvanic potential as the second member 110.

In this embodiment, the first opening 22 includes a centerline C1 that is substantially parallel to a centerline C2 of the first opening 32. This configuration provides for connected together first and second members 100, 110 that are substantially parallel.

The first and second coupling elements 20, 30 are constructed of material with the same or substantially the same galvanic potentials respectively as the first and second members 100, 110. Examples of the materials include but are not limited to titanium, titanium alloys, stainless steels, stainless steel alloys, cobalt chrome, and cobalt chrome alloys. In one embodiment, the first coupling element 20 is constructed from stainless steel, and the second coupling element 30 is constructed from titanium.

Figure 3:
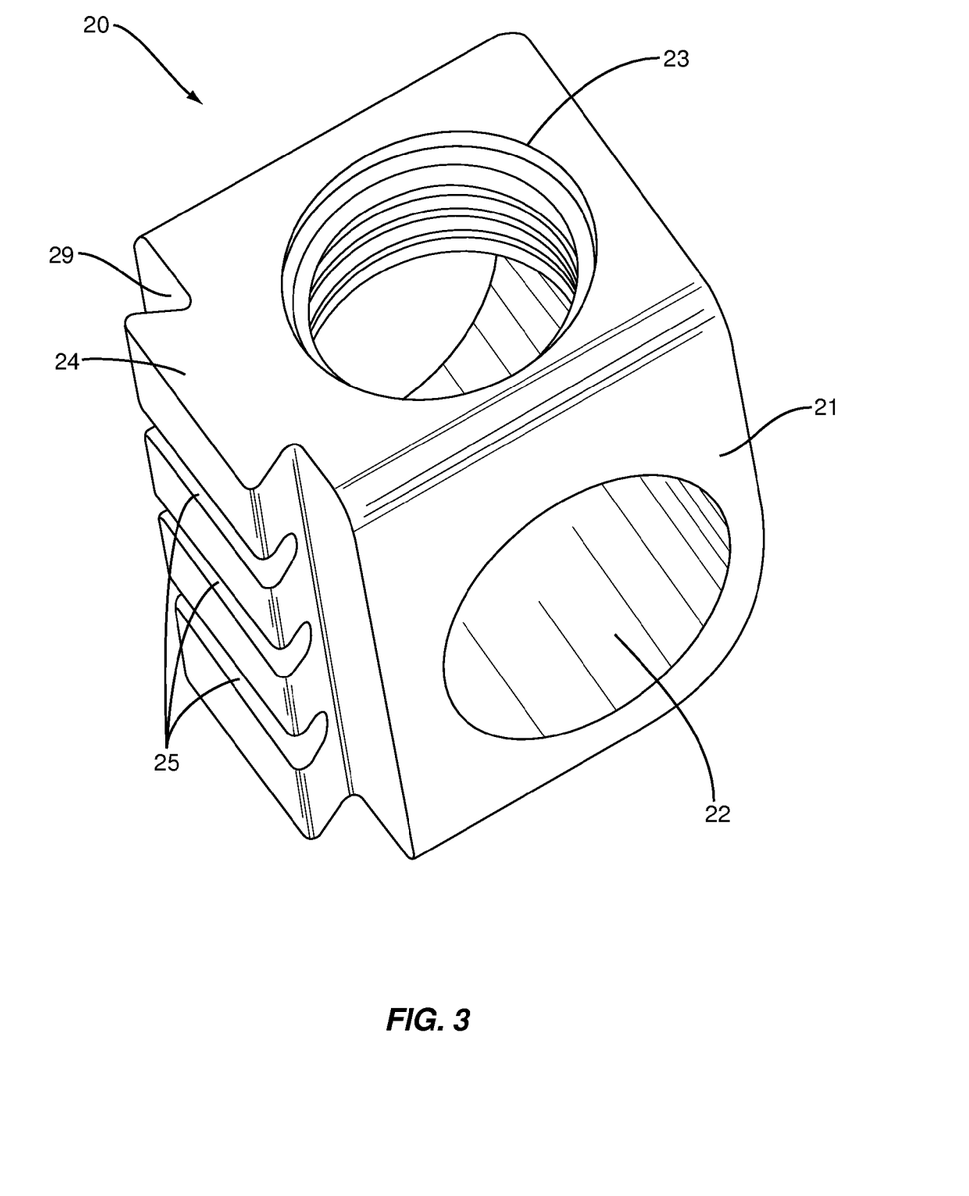
FIG. 3 is a perspective view of a coupling element constructed according to one embodiment.
Figure 4:
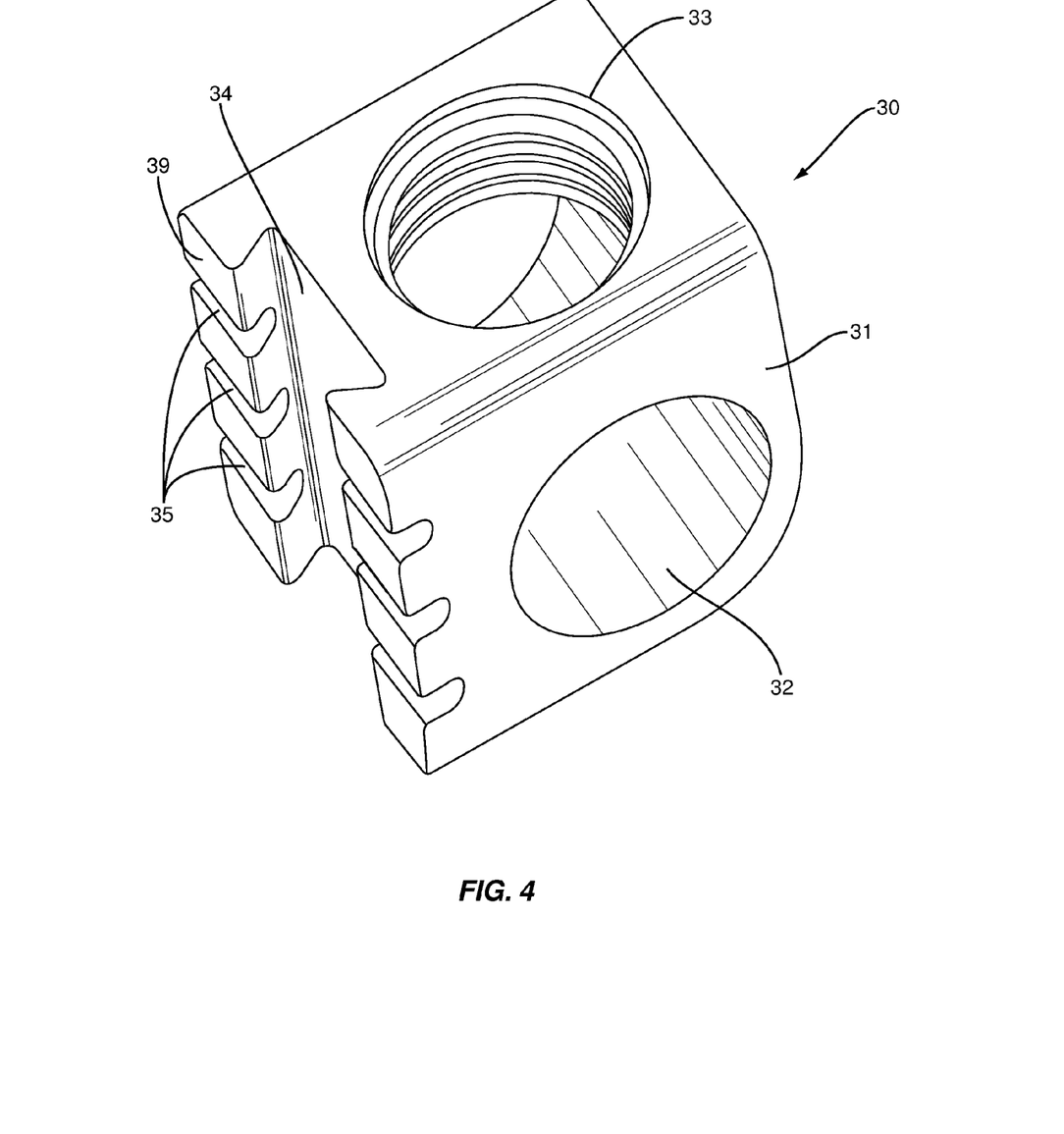
FIG. 4 is a perspective view of a coupling element constructed according to one embodiment.

The first and second coupling elements 20, 30 may be separate pieces as illustrated in FIGS. 3 and 4. FIG. 3 illustrates the first coupling element 20 that includes a contact side 29 that faces towards the second coupling element 30. The contact side 29 includes an outwardly-extending tongue 24. FIG. 4 illustrates the second coupling element 30 with a contact side 39 that faces towards the first coupling element 20. The contact side 39 includes a groove 34 that extends along the height of the body 31. Groove 34 includes a shape that accommodates the tongues 24. The tongues 24 are sized to fit within the groove 34 forming a dovetail connection between the coupling elements 20, 30. In another embodiment, the tongues 24 and groove 34 do not extend along the entirety of the contact sides 29, 39, but rather only along a limited length. Another embodiment includes a single tongue 24 that extends along the contact side 29. In another embodiment (not illustrated), the coupling medium 40 includes threads that engage with threads on the coupling elements 20, 30.

The coupling medium 40 is positioned between and forms a barrier that separates the first and second coupling elements 20, 30. Coupling medium 40 is constructed of an inert material that insulates the first and second coupling elements 20, 30. Coupling medium 40 includes a thickness that prevents the direct contact between the coupling elements 20, 30 that could produce galvanic corrosion. In one embodiment, the thickness of the medium 40 is substantially constant throughout. In other embodiments, the medium 40 includes a varying thickness. In each various embodiment, the coupling member 40 includes a thickness and is positioned across the contacts sides 29, 39 to prevent direct contact between the coupling elements 20, 30.

In one method of manufacturing the connector 10, the coupling elements 20, 30 are mated together with the tongue 24 positioned within the groove 34. The coupling medium 40 is initially in a flowable state and is injection molded to flow into the space formed between the coupling elements 20, 30. The medium 40 contacts against the contact surfaces 29, 39 and fills the space and eventually cures to a final state to connect together the coupling elements 20, 30.

Figure 5:
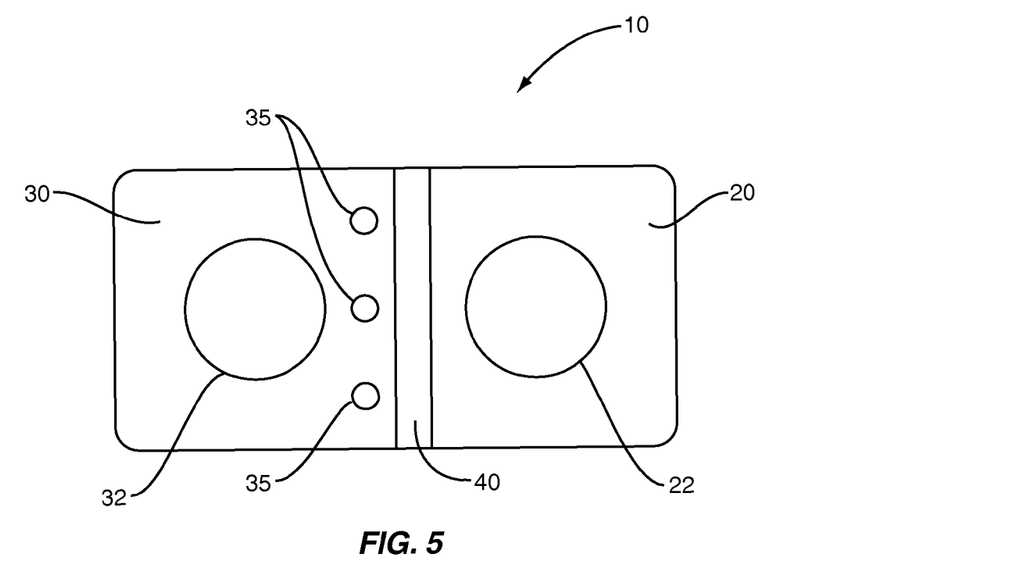
FIG. 5 is a side view of a connector constructed according to one embodiment.

In one embodiment, gaps 25 are positioned along the height of the contact surface 29. Similarly, gaps 35 are positioned along the contact surface 39. These gaps 25, 35 facilitate the insertion and flow of the coupling medium 40 during manufacturing. The coupling medium 40 fills the gaps 25, 35 to provide a secure attachment between the coupling elements 20, 30. In one embodiment as illustrated in FIGS. 2 and 4, gaps 35 extend inward from the contact surface 39. In another embodiment as illustrated in FIG. 5, gaps 35 are positioned inward from the contact surface 39 and extend inward into the groove (not illustrated in FIG. 5). The gaps 35 in each of these various embodiments are filled by the coupling medium 40 and form struts across the dovetail connection to prevent the coupling elements 20, 30 from sliding apart.

The coupling medium 40 may be constructed of a non-metallic material such as but not limited to PEEK (poly-ether-ether ketone), PEK, PAEK, PEKKEK, polymers, and/or ceramics and other non-conductive materials.

In one embodiment, the first member 100 is constructed of titanium and the second member 110 is stainless steel. The connector 10 includes a first coupling element 20 constructed of cobalt chrome that contacts against the titanium first member 100 and a second coupling element 30 constructed of stainless steel that connects to the stainless steel second member 110. The coupling medium 40 is constructed of PEEK that is positioned between the first and second coupling elements 20, 30.

Figure 6:
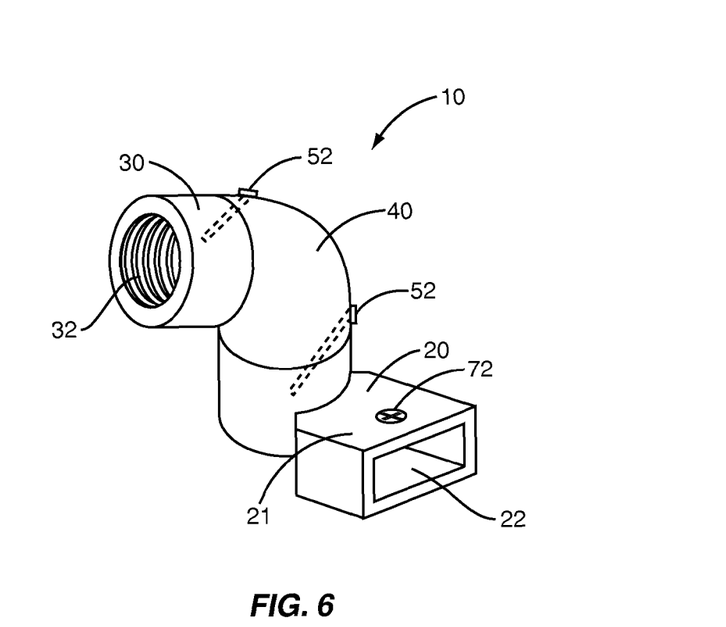
FIG. 6 is a perspective view of a connector constructed according to one embodiment.

FIG. 6 illustrates another embodiment of the device 10. In this embodiment, coupling element 20 includes a different shape than coupling element 30. Coupling element 20 includes an elongated first opening 22 to receive a first member such as a plate. A constraining mechanism 72 is positioned adjacent to the first opening 22 to constrain the first member 100. In this embodiment, constraining mechanism 72 includes a fastener that extends through an opening in the body 21. The constraining mechanism 72 contacts against the first member 100 positioned within the first opening 22 to prevent escape. Second coupling element 30 includes a substantially circular second opening 32 sized to receive the second member 110 in the form of a rod. In this embodiment, the first opening 22 is substantially perpendicular to the second opening 32.

The coupling medium 40 spaces apart the first and second coupling elements 20, 30. In one embodiment, the coupling medium 40 is attached to the coupling members 20, 30 with an adhesive. In another embodiment, fasteners 52 connect the coupling medium 40 to the coupling members 20, 30. In one embodiment as illustrated in FIG. 6, fasteners 52 extend between the coupling medium 40 and each of the coupling members 20, 30 for the attachment.

Figure 7:
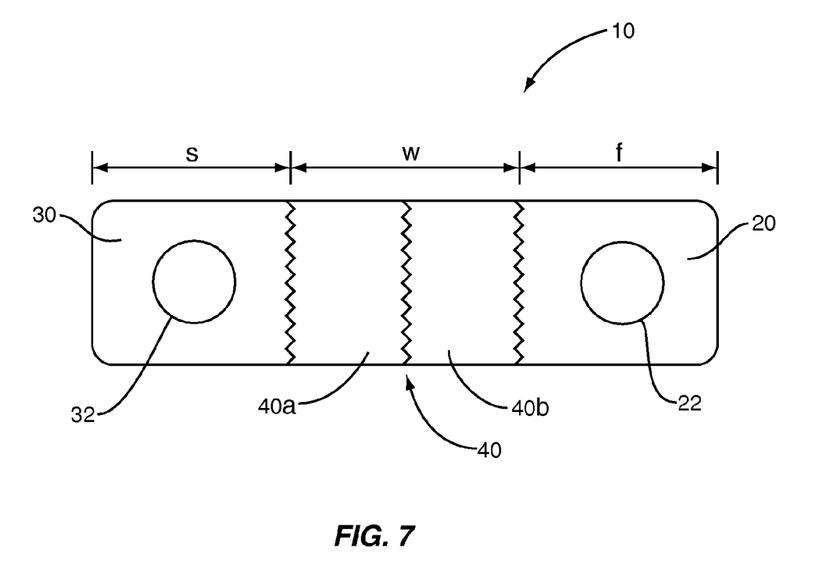
FIG. 7 is a side view of a connector constructed according to one embodiment.

FIG. 7 illustrates another embodiment of the device 10. This embodiment features the coupling medium 40 positioned directly between the first and second coupling members 20, 30. A width w of the coupling medium 40 is greater than a width f of the first coupling member 20 and a width s of the second coupling member 30.

In one embodiment, such as FIG. 5, coupling medium 40 is constructed from a single material. In another embodiment as illustrated in FIG. 7, coupling medium 40 is constructed of multiple different materials, such as first and second materials 40a, 40b. The different materials may be oriented to segregate the coupling members 20, 30.

Figure 8:
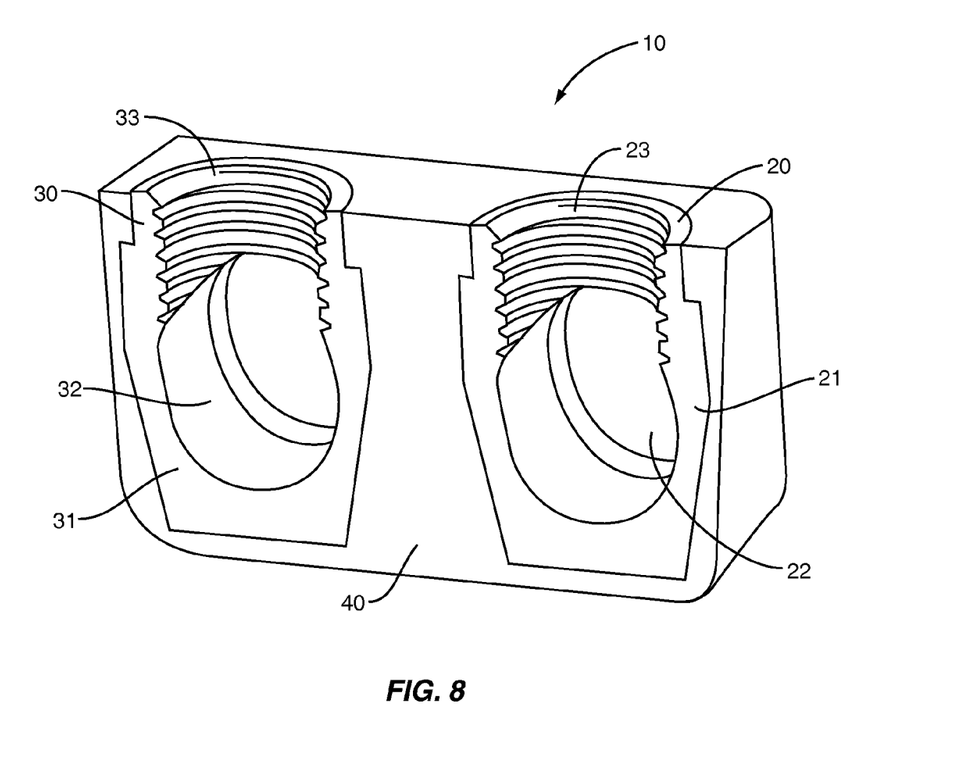
FIG. 8 is a section view of a connector constructed according to one embodiment.

FIG. 8 illustrates another embodiment with the coupling medium 40 substantially surrounding the first and second coupling members 20, 30. This construction again isolates the coupling members 20, 30 and inhibits galvanic corrosion. The coupling medium 40 surrounds the coupling members 20, 30 and forms and exterior of the device 10. Portions of the bodies 21, 31 may be exposed to the exterior to facilitate insertion of the first and second members 100, 110, or constraining elements 24, 34. In one embodiment, the coupling medium 40 is attached to the coupling members 20, 30 in an over-mold process. The bodies 21, 31 may be shaped to facilitate the molding process. One over-mold embodiment includes the coupling medium 40 being PEEK.

In one method of using the connector 10, the first member 100 is already implanted within a patient in a previous surgical procedure. A subsequent surgical procedure includes implanting the second member 110 and connecting the second member 110 to the first member 100. In some instances, the material of the first member 100 is unknown, or it is discovered during the subsequent surgical procedure to be constructed of a different material than originally expected. In these instances, the device 10 is connected between the first and second members 110, 110 to inhibit galvanic corrosion and provide a secure connection.

In another embodiment, the first and second members 100, 110 may be purposefully constructed of different materials. This occurs when the first member 100 includes one or more physical characteristics (e.g., stiffness, stress resistance, elasticity, hardness) for attachment within the patient at a first location, and the second member 110 includes one or more different physical characteristics for attachment at a second location. The device 10 allows for the two different members 100, 110 to be implanted within the patient.

The connector 10 may be used for connecting together a variety of different first and second members 100, 110. In one embodiment, first and second members 100, 110 are rods. Rods may include a variety of cross-sectional shapes, and may include a variety of lengths. One use of rods includes attachment to vertebral members to treat spinal deformities. Another use includes attachment to a broken bone, such as a femur, to support the broken bone and facilitate healing. First and second members 100, 110 may also include plates. Plates may include a working surface with a length and width that aligns with and contacts against bone. One or more apertures may extend through the plates to receive a fastener for securing to the bone. One example of a plate is a vertebral plate sized to fit against a vertebral member. In addition to the examples given above, connector 10 may also connect together cables and bars, and combinations of these various examples.

The embodiments of FIGS. 2, 3, and 4 include the openings 22, 32 extending through the bodies 21, 31 respectively. Other embodiments include one or both openings 22, 32 that do not extend completely through the bodies 21, 31.

The connector 10 may position the members 100, 110 at a variety of angular orientations including but not limited to parallel, perpendicular, and at non-perpendicular intersecting angles. Further, the connector 10 may position the members 100, 110 at various positional orientations including but not limited to end-to-end and overlapping.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present embodiments may be carried out in other specific ways than those herein set forth without departing from the scope and essential characteristics of the embodiments. The present embodiments are, therefore, to be considered in all respects as illustrative and not restrictive, and all changes coming within the meaning and equivalency range of the appended claims are intended to be embraced therein.

What is claimed is:

1. A connector for coupling together first and second surgical members of different materials, comprising:
   a first surgical member and a second surgical member having different galvanic potentials to one another;
   a first coupling element composed of a material with a same or similar galvanic potential to said first surgical member and including at least one male linking element along a coupling side;
   a second coupling element composed of a material with a same or similar galvanic potential to said second surgical member and including at least one female linking element along a corresponding coupling side; and
   a coupling medium of non-metallic material configured to have varying thickness disposed between said coupling side of said first coupling element and said corresponding coupling side of said second coupling element and connecting together said first and second coupling elements, said coupling medium preventing direct contact between the first and second coupling elements.

2. The connector of claim 1, wherein the coupling medium is PEEK (poly-ether-ether-ketone).

3. The connector of claim 1, wherein the first and second coupling elements are from the group of metals consisting of titanium, titanium alloys, stainless steel, stainless steel alloys, cobalt chrome and cobalt chrome alloys.

4. The connector of claim 1, wherein the coupling medium is an over-mold that surrounds both said first and second coupling elements.

5. The connector of claim 1, wherein the male linking element includes a dovetail displaced longitudinal along the coupling side.

6. The connector of claim 5, wherein the dovetail is intermittently interrupted with a first set of transverse slots.

7. The connector of claim 5, wherein the female linking element includes a detent displaced longitudinally along the corresponding coupling side and being sized to mate with the dovetail.

8. The connector of claim 7, wherein the detent is intermittently interrupted with a second set of transverse slots that are aligned with the first set of slots.

9. The connector of claim 1, wherein one of the first and second coupling elements is titanium, and the other of the first and second coupling elements is stainless steel, and the coupling medium is PEEK.

10. A connector for coupling together first and second surgical members of different materials, comprising:
   a first surgical member and a second surgical member having different galvanic potentials to one another;
   a first coupling element constructed of a first material that substantially matches a galvanic potential of the first surgical member, the first coupling element including a first opening to receive the first surgical member and a second opening in communication with the first opening to receive a constraining member, the first coupling element further including a contact surface;
   a second coupling element constructed of a second material that substantially matches a galvanic potential of the second surgical member, the second coupling element including a first opening to receive the second surgical member and a second opening in communication with the first opening to receive a constraining member, the second coupling element further including a contact surface; and a non-metallic coupling medium configured to have varying thickness positioned between the first and second coupling elements and in contact with the contact surfaces, the coupling medium including a width to space apart the contact surfaces.

11. The connector of claim 10, wherein the first and second coupling elements interlocking members that extend outward from each of the contact surfaces.

12. The connector of claim 10, wherein the first openings of the first and second coupling elements are substantially parallel.

13. A system comprising:
a first surgical member and a second surgical member having different galvanic potentials to one another;
a first coupling element with a galvanic potential similar to one of the first and second surgical members;
a second coupling element with a galvanic potential similar to the other surgical members; and
a non-metallic coupling medium made of at least two different materials disposed between and separating said first and second coupling elements and joining the first and second coupling elements together.

14. The system according to claim 13, wherein the non-metallic coupling medium is PEEK, the first coupling element is stainless steel and the second coupling element is titanium.

15. The system according to claim 14, wherein the PEEK coupling medium is applied with an over-mold to the first and second coupling elements.

16. The system according to claim 13, wherein the first coupling element includes a longitudinally running dovetail intermittently dispersed with a first set of slots.

17. The system according to claim 16, wherein the second coupling element includes a longitudinally running detent intermittently dispersed with a second set of slots that are aligned with the first set of slots.

18. The system according to claim 17, where in the coupling medium is disposed within the first and second set of slots and the dovetail.

19. The system according to claim 13, wherein the first and second coupling elements are from the group of metals consisting of titanium, titanium alloys, stainless steel, stainless steel alloys, cobalt chrome and cobalt chrome alloys.

20. A method for connecting together two surgical members of different galvanic potentials comprising:
providing a connector for coupling together a first surgical member and a second surgical member according to claim 1;
providing the first coupling element of similar galvanic potential to one of the surgical members;
providing the second coupling element of similar galvanic potential to the other surgical members; and
interlocking said first coupling element to said second coupling element using the non-metallic coupling medium.

21. The method of claim 20, wherein the coupling medium is PEEK.

22. The method of claim 20, wherein the step of interlocking said first coupling element to said second coupling element includes mating a dovetail on the first coupling element with a detent on the second coupling element.

23. The method of claim 22, wherein both the detent and the dovetail include intermittently dispersed transverse slots.

* * * * *